(12) United States Patent
Lee et al.

(10) Patent No.: US 7,671,522 B2
(45) Date of Patent: Mar. 2, 2010

(54) LARGE-AREA SHOWER ELECTRON BEAM IRRADIATOR WITH FIELD EMITTERS AS AN ELECTRON SOURCE

(75) Inventors: Byung-Cheol Lee, Daejeon (KR); Young-Kyung Lim, Daejeon (KR); Young-Hwan Han, Daejeon (KR); Young-Uk Jung, Daejeon (KR); Seong-Hee Park, Daejeon (KR); Cheol-Jin Lee, Seoul (KR); Tae-Jae Lee, Choongchunbook-do (KR)

(73) Assignee: Korea Atomic Energy Research Institute (KR)

( * ) Notice: Subject to any disclaimer, the term of this patent is extended or adjusted under 35 U.S.C. 154(b) by 480 days.

(21) Appl. No.: 10/591,894

(22) PCT Filed: Mar. 9, 2005

(86) PCT No.: PCT/KR2005/000650

§ 371 (c)(1),
(2), (4) Date: May 1, 2007

(87) PCT Pub. No.: WO2005/086201

PCT Pub. Date: Sep. 15, 2005

(65) Prior Publication Data

US 2007/0278928 A1      Dec. 6, 2007

(30) Foreign Application Priority Data

Mar. 9, 2004      (KR) ..................... 10-2004-0015693

(51) Int. Cl.
  *H01J 19/50*      (2006.01)
  *H01J 1/24*       (2006.01)

(52) U.S. Cl. ....................... 313/289; 313/420

(58) Field of Classification Search ................. 313/326, 313/283, 289, 252, 239, 244, 253, 255, 420, 313/317, 331, 361.1; 250/306; 315/94
See application file for complete search history.

(56) References Cited

U.S. PATENT DOCUMENTS 3,416,980 A      12/1968    Cahen et al.

(Continued)

FOREIGN PATENT DOCUMENTS

DE          4002049 A1        7/1991

(Continued)

*Primary Examiner*—Karabi Guharay
*Assistant Examiner*—Sheryl Hull
(74) *Attorney, Agent, or Firm*—The Webb Law Firm

(57) ABSTRACT

An electron beam irradiator capable of performing electron beam irradiation in a wide area at a high current density with a field emitter tip. The electron beam irradiator comprises: a vacuum chamber having a beam irradiation window formed longitudinally in an outer periphery of the vacuum chamber; a cathode placed centrally and longitudinally inside the vacuum chamber, and having a field emitter tip formed on the cathode, corresponding to the beam irradiation window; and a high voltage supply placed at one end of the vacuum chamber, and adapted to apply high voltage toward the cathode. The electron beam irradiation can be made in a wide area without using an electromagnet as well as in a high current density without using a heater such as a filament or an additional power supply, thereby to ensure a simplified structure as well as a reduced size.

15 Claims, 6 Drawing Sheets

U.S. PATENT DOCUMENTS

| | | | |
|---|---|---|---|
| 3,769,600 A | 10/1973 | Denholm et al. | |
| 3,978,363 A * | 8/1976 | Bayless | 313/289 |
| 4,008,413 A * | 2/1977 | Bayless | 313/331 |
| 5,729,583 A | 3/1998 | Tang et al. | |
| 5,877,588 A | 3/1999 | Kaftanov et al. | |
| 7,078,716 B2 * | 7/2006 | Fink et al. | 250/492.3 |
| 2003/0062488 A1 | 4/2003 | Fink et al. | |
| 2004/0256975 A1 * | 12/2004 | Gao et al. | 313/495 |
| 2005/0225224 A1 * | 10/2005 | Dally et al. | 313/361.1 |

FOREIGN PATENT DOCUMENTS

| | | |
|---|---|---|
| JP | 7-282755 A | 10/1995 |
| JP | 9-166699 A | 6/1997 |
| JP | 10-62600 A | 3/1998 |
| JP | 2002228800 | 8/2002 |
| JP | 2004-047254 A | 2/2004 |
| WO | 9857345 A1 | 12/1998 |

* cited by examiner

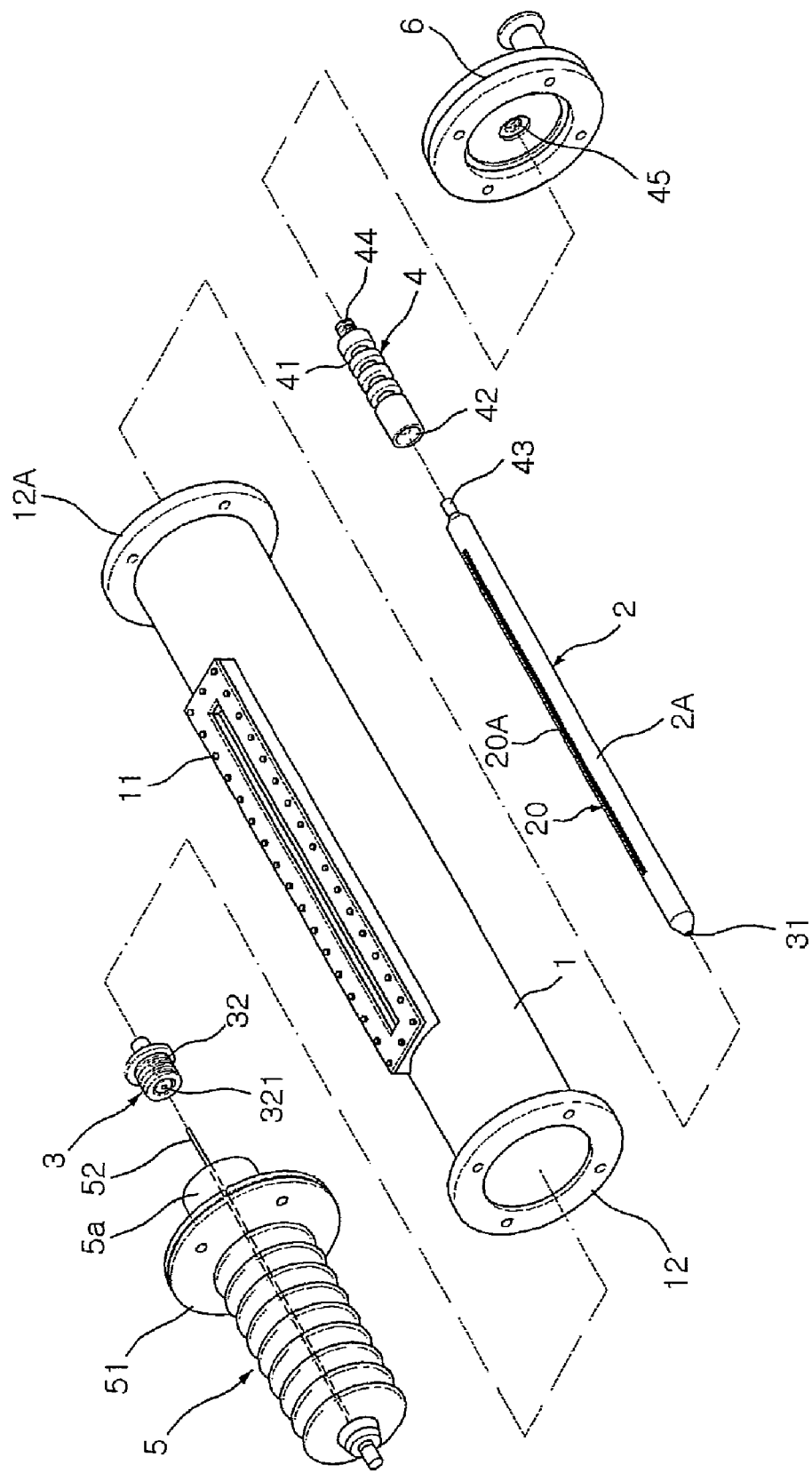
[Fig. 1]

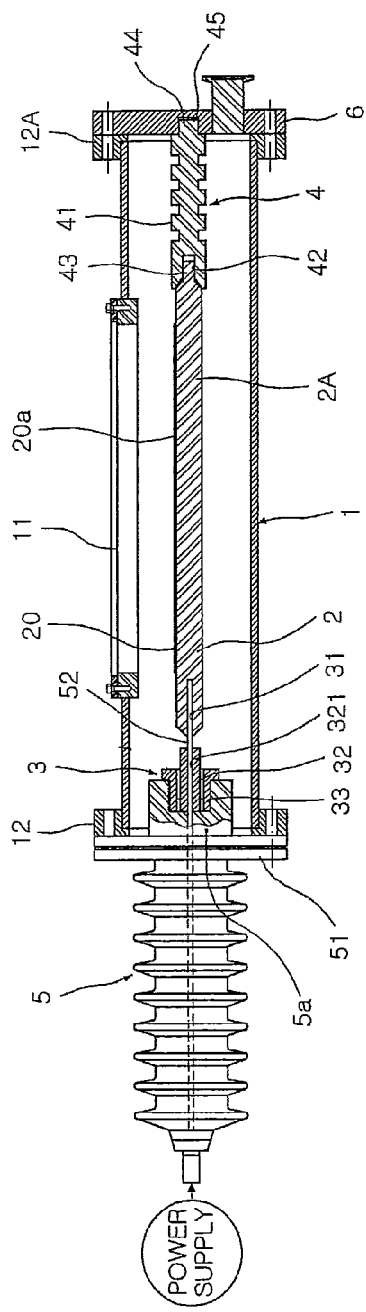
[Fig. 2]
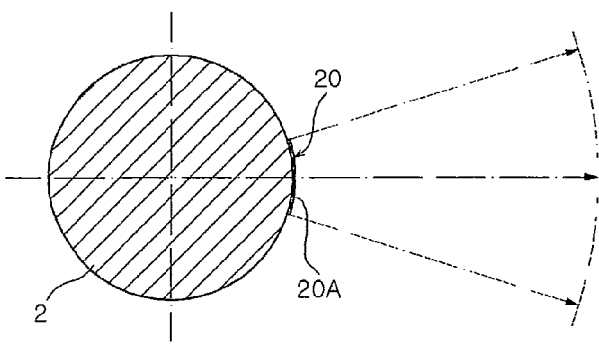
[Fig. 3]

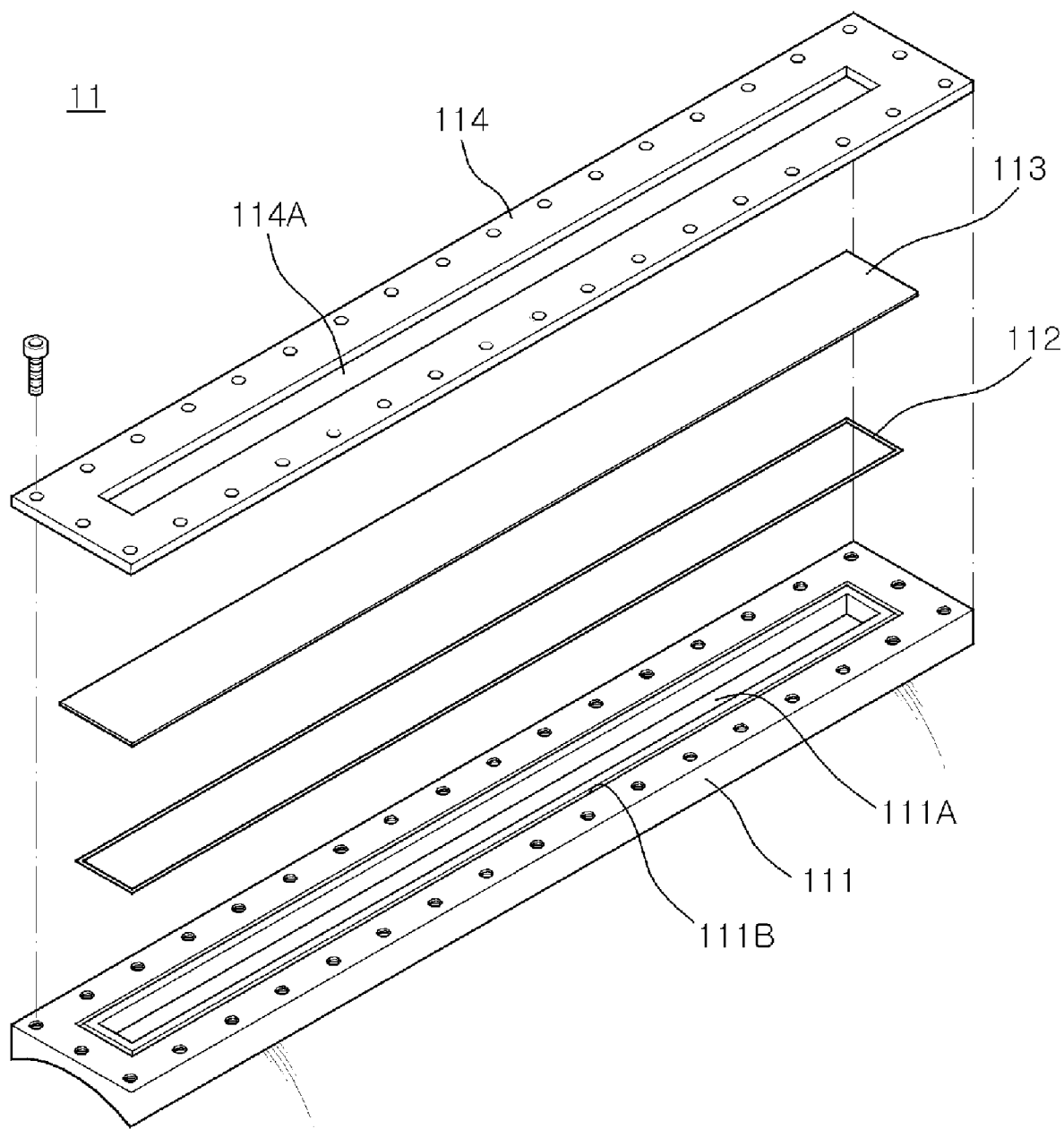
[Fig. 4]

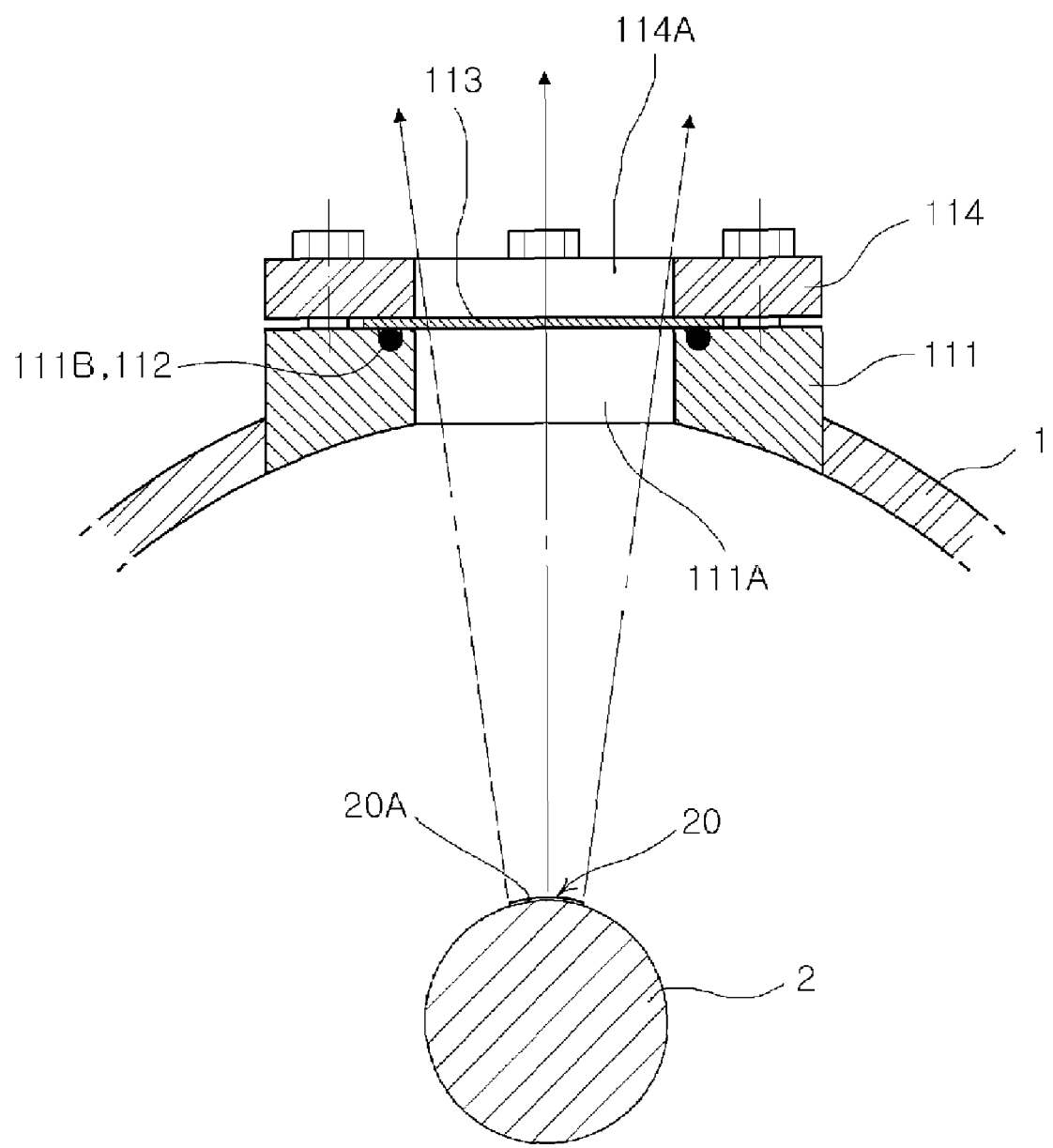
[Fig. 5]

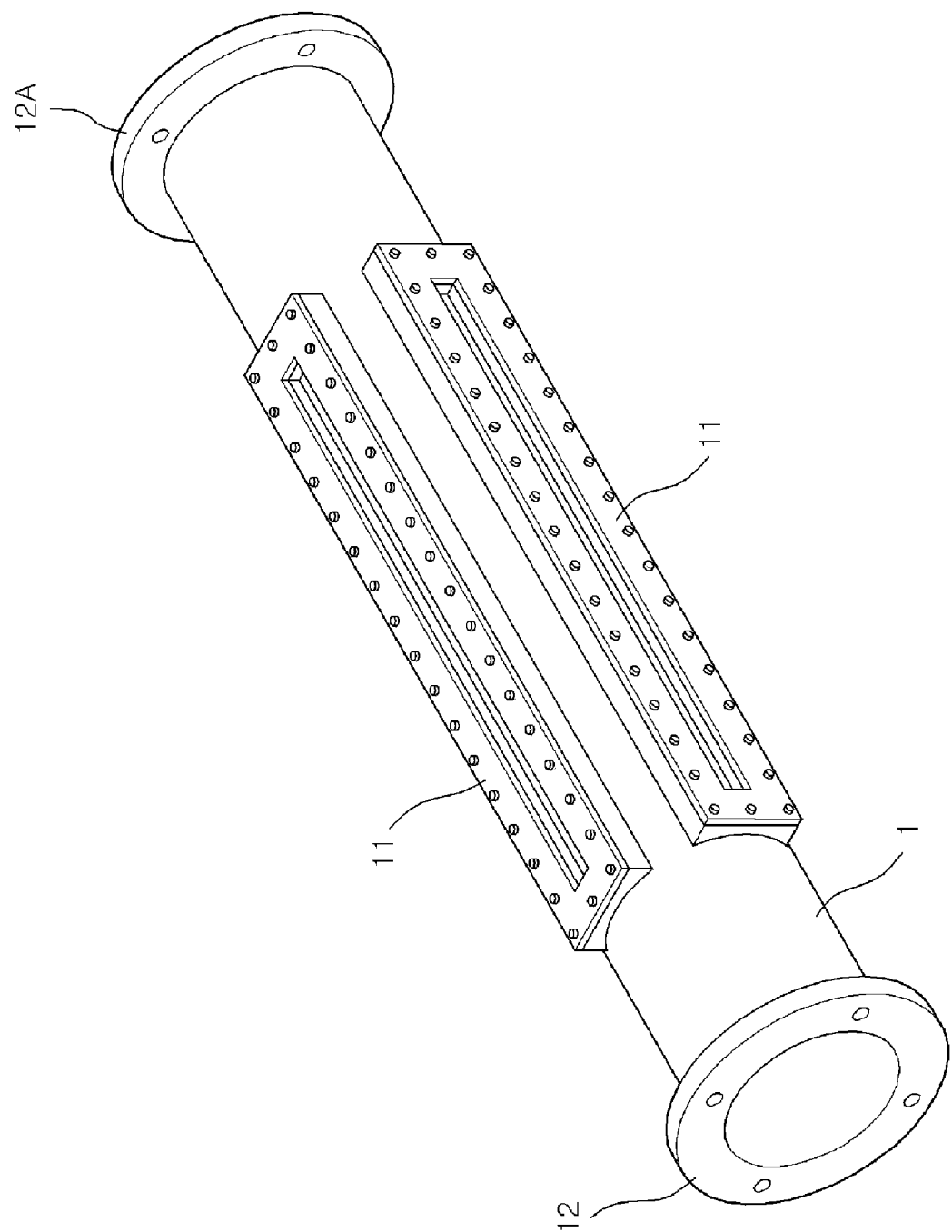
[Fig. 6]

[Fig. 7]
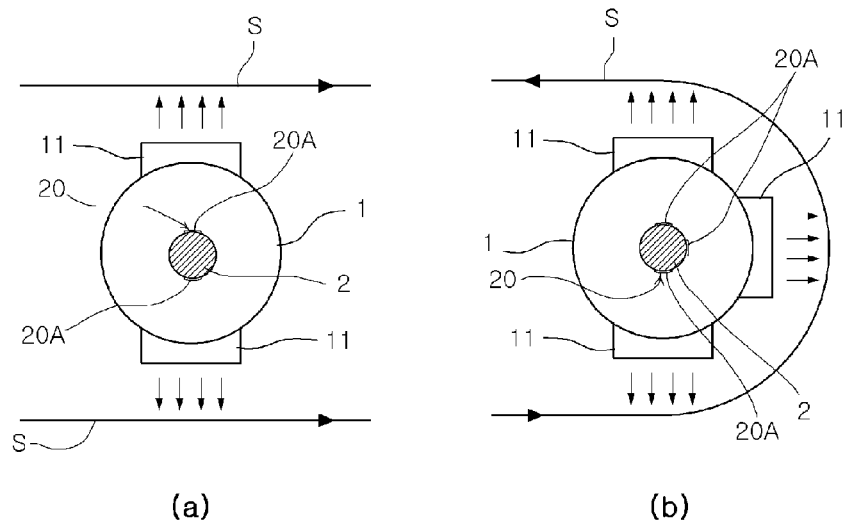
(a)  (b)
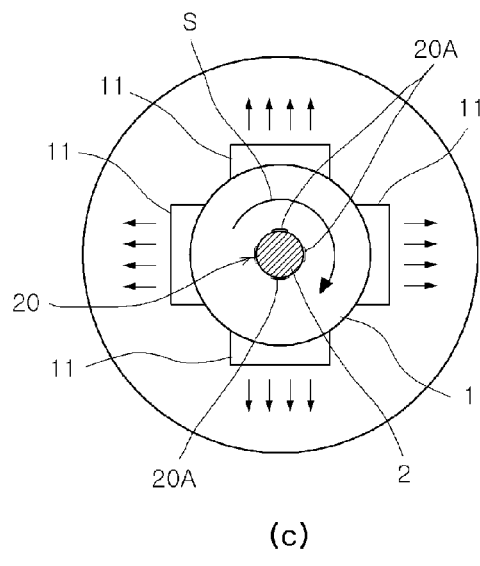
(c)
[Fig. 8]
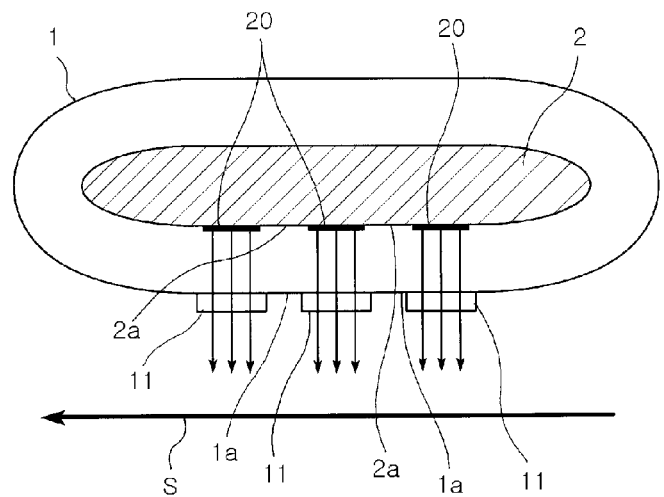

LARGE-AREA SHOWER ELECTRON BEAM IRRADIATOR WITH FIELD EMITTERS AS AN ELECTRON SOURCE

TECHNICAL FIELD

The present invention relates to an electron beam irradiator, and more particularly, a low-energy electron beam irradiator designed to allow electron beam irradiation in a wide area without using a scanning magnet system as well as in a high current density without using a heater such as a filament or an additional power supply, thereby to ensure a simplified structure as well as a reduced size.

BACKGROUND ART

As well known to those skilled in the art, the property of every substance is determined by the bonding of component atoms, in which the bonding is carried out by outer electrons bound to the atoms. Changing the bonding status of a substance with electron beams of a sufficient energy level can obtain a property totally different from the previous one can be realized.

That is, electron beams may be irradiated to a substance to give an additional available property to it or to remove any property, for example, harmful to the human from it.

A cathode material used in an electron beam irradiator to generate electron beams is generally selected from various single crystals, oxides and so on that has a low work function. However, these materials are restricted in their size to use an e-beam irradiator sources, and thus the use of an electromagnet is necessary in order to give electron beams irradiation and treatment to an object in a wide area.

Besides, conventional electron beam irradiators are of thermoelectric actuation type in which a cathode material is heated with a filament up to a suitable high temperature in order to produce electron beams. This as a result essentially needs an additional separate power supply to be used together with the filament.

OBJECTS OF THE INVENTION

As described above, conventional electron beam irradiators have a complicated structure. Besides, since conventional electron beam irradiation is carried out with a point electron beam source, there are drawbacks in that irradiation efficiency degrades and economic competitiveness and workability become poor.

Accordingly, an electron beam irradiator capable of preventing the above problems has been required in the art.

The present invention has been made to solve the foregoing problems of the prior art and it is therefore an object of the present invention to provide an electron beam irradiator designed to irradiate electron beams in a wide area without using an electromagnet system as well as in a high current density without using a heater such as a filament or an additional power supply, thereby to ensure a simplified structure as well as a reduced size.

It is another object of the invention to provide an electron beam irradiator designed to irradiate electron beams radially from a strip-shaped field emitter tip of a cathode allowing a larger area to be irradiated at a wider area, thereby further improving the irradiation efficiency of electron beams.

It is further another object of the invention to provide an electron beam irradiator designed to be simply assembled and disassembled thereby enhancing the promptitude, simplicity and efficiency of assembly, substitution and maintenance.

It is other object of the invention to provide an electron beam irradiator designed to minimize the distortion of an accelerated electric field of electron beams irradiated through a beam irradiation window while preventing the vacuum state of a vacuum chamber from damage through the beam irradiation window as well as to achieve a sufficient enduring force against the pressure difference between the vacuum and the air while minimizing the thickness of a metal foil through which the electron beams are irradiated thereby to decrease the loss of the electron beams and resultant energy loss through the metal foil.

It is yet another object of the invention to provide an electron beam irradiator designed to form several beam irradiation windows in a single cylindrical unit in order to ensure independent application and high operation efficiency for the respective beam irradiation windows according to use, further raise treatment efficiency for the inside of a cylindrical object in particular, and enable current density adjustment according to the distance change between the irradiator and the object.

SUMMARY OF THE INVENTION

According to an aspect of the invention for realizing the above objects, it is provided an electron beam irradiator comprising: a vacuum chamber having a beam irradiation window formed longitudinally in an outer periphery of the vacuum chamber; a cathode placed centrally and longitudinally inside the vacuum chamber, and having a field emitter tip formed on the cathode, corresponding to the beam irradiation window; a high voltage supply placed at one end of the vacuum chamber, and adapted to apply high voltage toward the cathode; a first support including a pin insert hole formed at one end of the cathode and a first insulator formed in the high voltage supply for the passage of a high voltage supply pin so that the high voltage supply pin is inserted into the pin insert hole of the cathode through the first insulator; and a second support including an insert groove formed in a second insulator longitudinally and axially located at the other end of the cathode so that an insert protrusion formed at the other end of the cathode is inserted into the insert groove to support the cathode.

Preferably, the field emitter tip is made of a carbon nanotube.

In the invention, the cathode is of a rod-shaped structure having a circular cross-section, and includes a field emitter tip shaped as a strip formed longitudinally in an outer periphery of the rod-shaped structure.

The electron beam irradiator may further comprise: fixing flanges integrally provided at both ends of the vacuum chamber; a first vacuum flange coupled with one of the fixing flanges, and having a high voltage supply; a second vacuum flange coupled with the other one of the fixing flanges; a first support including a pin insert hole formed at one end of the cathode and a first insulator formed in the high voltage supply for the passage of a connector pin of the high voltage supply so that the connector pin is inserted into the pin insert hole of the cathode through the first insulator; and a second support including an insert groove formed in a second insulator longitudinally and axially in a central potion of the second vacuum flange so that an insert protrusion formed at the other end of the cathode is inserted into the insert groove to support the cathode.

In the invention, the beam irradiation window may comprise: a base plate fixed to the vacuum chamber, slightly protruded from the vacuum chamber to the outside, and having an elongated rectangular slit formed in a central area thereof; a metal wire inserted into an insert groove formed in an outer periphery of the slit of the base plate; a metal foil placed on the metal wire, and having an area slightly larger than an area surrounded by the metal wire; and a cover plate coupled with the base plate, corresponding to the slit of the base plate, and having a beam irradiation slit corresponding to the slit in the central area of the base plate.

Preferably, the vacuum chamber is cylindrical, with a plurality of beam irradiation windows formed in an outer periphery thereof, and wherein the cathode placed inside the vacuum chamber has field emitter tips formed in an outer periphery of the cathode, corresponding to the beam irradiation windows of the vacuum chamber, respectively.

According to another aspect of the invention for realizing the above objects, it is provided an electron beam irradiator comprising: a vacuum chamber having a plurality of beam irradiation windows formed longitudinally in an outer peripheral area of the vacuum chamber; a cathode placed inside the vacuum chamber, and having at least one linear area formed thereon and a plurality of field emitter tips formed on the linear area, corresponding to the beam irradiation windows, respectively; and a high voltage supply placed at one end of the vacuum chamber, and adapted to apply high voltage toward the cathode.

Preferably, the vacuum chamber has at least one linear area opposed in parallel to the linear area of the cathode, in which the beam irradiation windows are formed.

As described above, the present invention provides an electron beam irradiator designed to irradiate electron beams in a wide area at a low energy by using field emitter tips so that electron beams can be irradiated in a wide area without using an electromagnet as well as in a high current density without using a heater such as a filament or an additional power supply, thereby ensuring a simplified structure as well as a reduced size.

Also, according to the invention, the electron beam irradiator, by using electron beams emitted from strip-shaped field emitter tips formed in a cathode, can rapidly cure ink or paint applied in a wide area as well as facilitates massive disinfection and sterilization of medical articles.

Besides, according to the invention, the electron beam irradiator can be simply assembled and disassembled thereby enhancing the promptitude, simplicity and efficiency of assembly, substitution and maintenance.

In addition, according to the invention, the electron beam irradiator can minimize the distortion of an accelerated electric field of electron beams irradiated through a beam irradiation window while preventing the vacuum state of a vacuum chamber from damage through the beam irradiation window as well as to achieve a sufficient enduring force against the pressure difference between the vacuum and the air while minimizing the thickness of a metal foil through which the electron beams are irradiated thereby to decrease the loss of the electron beams and resultant energy loss through the metal foil.

Furthermore, according to the invention, the electron beam irradiator can form several beam irradiation windows in a single cylindrical unit in order to ensure independent application and high operation efficiency for the respective beam irradiation windows according to use, further raise treatment efficiency for the inside of a cylindrical object in particular, and enable current density adjustment according to the distance change between the irradiator and the object.

BRIEF DESCRIPTION OF THE DRAWINGS

The above and other objects, features and advantages of the present invention will be more clearly understood from the following detailed description taken in conjunction with the accompanying drawings, in which:

FIG. 1 is an exploded perspective view illustrating an electron beam irradiator according to an embodiment of the invention;

FIG. 2 is a cross-sectional view illustrating an assembled state of the electron beam irradiator shown in FIG. 1;

FIG. 3 is a cross-sectional view illustrating an electron beam irradiation pattern according to the invention;

FIG. 4 is an exploded perspective view illustrating an electron beam irradiation window according to the invention;

FIG. 5 is a cross-sectional view illustrating an assembled state of the electron beam irradiation window shown in FIG. 4;

FIG. 6 is a perspective view illustrating an electron beam irradiator according to another embodiment of the invention;

FIGS. 7a to 7c illustrate electron beam irradiation patterns from the electron beam irradiator as shown in FIG. 6 according to the invention, in which FIG. 7a is an illustration of a plurality of beam irradiation windows provided according to the invention, in which independent irradiation is performed, FIG. 7b is an illustration of beam irradiation windows provided at three sides according to the invention, in which multiple irradiation is performed onto an object moving on a curved surface, and FIG. 7c is an illustration of beam irradiation windows provided at four sides according to the invention, in which multiple irradiation is performed onto the inside surface of a cylindrical object; and FIG. 8 is an illustration of the operation state of an electron beam irradiator according to yet another embodiment of the invention.

DETAILED DESCRIPTION OF THE INVENTION

Preferred embodiments of the invention will be described in more detail in conjunction with the accompanying drawings.

FIG. 1 is an exploded perspective view illustrating an electron beam irradiator according to an embodiment of the invention, as will be described hereinafter.

As shown in FIG. 1, the electron beam irradiator of the invention includes an electrically-anodic vacuum chamber 1, which is adapted to keep the inside in vacuum, a cathode 2 centered longitudinally inside the vacuum changer 1 and having a rod-shaped structure 2A, first and second supports 3 and 4 supporting both ends of the cathode 2 inside the vacuum changer 1, respectively, and a high voltage supply 5 for applying high voltage to the cathode 2.

The vacuum chamber 1 may be of a cylindrical structure with opening at both ends, and has an elongated beam irradiation window 11 formed in a substantially middle area in the outer periphery of the cylindrical structure. In addition, first and second fixing flanges 12 and 12A are formed integral with the both ends of the vacuum chamber 1.

The cathode 2 is shaped as an elongated rod with a circular cross section. A field emitter tip 20 shaped as an elongated strip is formed on the cathode 2, opposed to the beam irradiation window 11 in the vacuum chamber 1. The field emitter tip 20 is preferably made of carbon nanotubes 20A.

Carbon nanotubes were found by Dr. Iijima Suimo of NEC Corporation's Fundamental Research Laboratory in 1991 when he was analyzing carbon solids grown on a graphite cathode by using electric discharge, in which hexagons of six carbon atoms are connected together into the shape of a tube having a diameter on the order of merely from several to several tens of nanometers. This is also called as a field emitter tip. By way of additional background, a nanometer measures $1/1,000,000,000$ m which is substantially equal to $1/100,000$ of a human hair.

Carbon nanotubes exhibit electrical conductivity as high as copper, thermal conductivity as high as diamond, which has been known having the most excellent strength in the nature, and strength 100 times greater than steel. Carbon nanotubes can endure up to 15% deformation whereas carbon fibers are cut at merely 1% deformation. In the invention, carbon nanotubes are adopted as an electron beam irradiator.

When the carbon nanotubes 20A are applied with high voltage, it emits high current density electron beams through field emission.

The high voltage supply 5 of the invention is adapted to hermetically seal the both openings of the vacuum chamber 1 as well as apply high voltage to the cathode 2.

The electron beam irradiator of the invention includes a first vacuum flange 51 coupled with the first fixing flange 12 of the vacuum chamber 1 and a second vacuum flange 6 fixed to the second fixing flange 12A of the chamber 1 in order to hermetically seal the vacuum chamber 1 from the outside. The vacuum flanges 51 and 6 are sealed through bolt fastening.

Besides, in the electron beam irradiator of the invention, the first and second supports 3 and 4 are adapted to support the cathode 2 at both ends thereof inside the vacuum chamber 1. The first support 3 includes a pin insert hole 31 formed at one end of the cathode 2, as shown in FIG. 2, for receiving a connector pin 52 protruded from the high voltage supply 5 therein so as to provide electrical connection to the cathode 2 while supporting them in position.

The first support 3 has a first insulator 32 shaped to surround the connector pin 52 and made of insulation ceramic. The first insulator 32 has a pin through hole 321 in a central portion thereof, which allows the passage of the connector pin 52 of the high voltage supply 5. The outer surface of the first insulator 32 is screwed into a mounting groove 33 provided in an insulator 5a of the high voltage supply 5.

This insulation structure ensures that high voltage flowing along the connector pin 52 is positively, electrically insulated from other components other than the cathode 2.

The second support 4 includes a coupling groove 45 formed in a central portion of the second vacuum flange 6 and a second insulator 41 with a coupling protrusion 44 in its rear end. The rear coupling protrusion 44 is adapted to be spirally coupled with the coupling groove 45.

Besides, the second insulator 41 has an insert groove 42 formed in a front central portion thereof, and the cathode 2 has an insert protrusion 43 to be inserted into the insert groove 42 and supported therein.

In addition, it is preferable that a number of prominences and depressions are formed in the surface of the first and second insulators 32 and 41 extending surface passages thereof in order to prevent insulation breakdown under high voltage.

FIG. 2 is a cross-sectional view illustrating an assembled state of the electron beam irradiator shown in FIG. 1, as will be described hereinafter.

In the electron beam irradiator of the invention, the cathode 2 is provided longitudinally in a central portion of the vacuum chamber 1, in which one end of the cathode 2 is connected with the high voltage supply 5 by the first support 3 and supported in position thereby, whereas the other end of the cathode 2 is connected with the second vacuum flange 6 by the second support 4 and supported in position thereby. The one end of the cathode 2 is supported as the connector pin 52 of the high voltage supply 5 is inserted into the pin insert hole 31 of the cathode 2 through the first insulator 32 of the support 3, and the other end of the cathode 2 is supported as the rear insert protrusion 43 of the cathode 2 is inserted into the insert groove 42 of the second insulator 41.

The connector pin 52 is electrically connected to a power supply (not shown) via the high voltage supply 5 so that high voltage supplied from the power supply is applied to the cathode 2.

In the electron beam irradiator of the invention structured as above, when high voltage is applied to the cathode 2, the field emitter tip 20 provided opposite to the beam irradiation window 11 of the vacuum chamber 1 emits electron beams of high current density via field emission. Since the cathode 2 has a circular cross-section and the field emitter tip 20 is formed along the curve of the circular cross-section, electron beams are radially generated as shown in FIG. 3.

The electron beams are then accelerated with a predetermined energy between the vacuum chamber 1, electrically acting as an anode, and the cathode 2, such that the accelerated electron beams are irradiated through the beam irradiation window 11 of the vacuum chamber 1.

FIGS. 4 and 5 illustrate the electron beam irradiation window equipped in the electron beam irradiator of the invention, as will be described hereinafter.

The electron beam irradiation window 11 is provided in the vacuum chamber 1, and has a base plate 111 formed in an elongated, substantially rectangular opening of the vacuum chamber 1. The base plate 111 is integrally protruded from the vacuum chamber 1. An elongated rectangular slit 111A is formed in a central portion of the base pin 111, and a substantially rectangular wire insert groove 111B is formed in the outer circumference of the slit 111A, by which a metal wire 112 is received in the base plate 111.

A thin metal foil 113 is seated on the metal wire 112, and a cover plate 114 is placed on the metal foil 113 and coupled with the base plate 111 via bolt fastening. In a central portion of the cover plate 114, a beam irradiation slit 114A having a shape matching that of the slit 111A of the base plate 111.

The base plate 111 is preferably designed to protrude at a minimum dimension in order to decrease the distortion of an accelerated electric field. The metal wire 112 acts as a seal to prevent the vacuum inside the vacuum chamber 1 from being lost through the beam irradiation window 11.

In the beam irradiation window 11 equipped in the electron beam irradiator of the invention structured as above, the thin metal foil 113 can positively withstand the pressure difference between the vacuum and the air since the slit A in the base plate 111 has a small width. This as a result can relatively increase the quantity of electron beams penetrating the metal foil 113 over those of penetrating a thick metal foil, thereby decreasing energy loss. So, advantageously, the beam irradiation window 11 can act as a suitable beam irradiation window for low energy electron beams.

FIG. 6 is a perspective view illustrating an electron beam irradiator according to another embodiment of the invention. As shown in FIG. 6, the electron beam irradiation of the invention has a plurality of beam irradiation windows 11 around a vacuum chamber 1. Also, a cathode 2 is provided longitudinally, centrally inside the vacuum chamber 1, and has a plurality of field emitter tips 20 matching the beam irradiation windows 11, respectively.

That is, the plural beam irradiation windows 11 are provided in a single electron beam irradiator of the invention so that the individual beam irradiation windows 11 can be used simultaneously, separately with different use as shown in FIGS. 7a to 7c. Besides, it is effective to provide treatment to the inner surface of a cylindrical object, and by radially irradiating electron beams, current density can be adjusted according to change in the distance between the irradiator and the object.

As shown in FIG. 7a, with the beam irradiation windows 11 formed at both sides of the vacuum chamber 1, the electron beam irradiator of the invention can provide treatment to objects while they linearly move along arrows S outside the vacuum chamber 1. Also, as shown in FIG. 7b, with the three beam irradiation windows 11 provided at three sides of the vacuum chamber 1, the electron beam irradiator can provide treatment to an object which linearly moves around the beam irradiation windows 11 in the direction of an arrow S.

In addition, as shown in FIG. 7c, the four beam irradiation windows 11 formed at four sides of the vacuum chamber 1, the electron beam irradiator of the invention can provide treatment to a cylindrical object while being rotated in the direction of an arrow S inside a cylindrical object.

Since mechanisms for rotating the vacuum chamber 1 can be readily made by using a rotary motor (not shown) and a power transmission (not shown), which are common in the art, they will not be described in detail.

FIG. 8 is an illustration of the operation state of an electron beam irradiator according to yet another embodiment of the invention.

The electron beam irradiator of the invention shown in FIG. 8 includes a vacuum chamber 1 with a plurality of beam irradiation windows 11 formed longitudinally on the vacuum chamber 1.

The vacuum chamber 1 preferably has a linear area 1a on the outer surface, on which the beam irradiation windows 11 are formed.

Inside the vacuum chamber 1, a cathode 2 having a plurality of field emitter tips 20 is provided. The cathode 2 has at least one linear area 2a opposed in parallel to the linear area 1a of the vacuum chamber 1. On the linear area 2a, the field emitter tips 20 are placed corresponding to the beam irradiation windows 11, respectively. In addition, a high voltage supply (not shown) for applying high voltage toward the cathode 2 is provided in the vacuum chamber 1.

The field emitter tips 20 are preferably made of carbon nanotubes 20A.

The electron beam irradiator of the invention can advantageously treat an object outside the vacuum chamber 1 while the object linearly moves along the linear area 1a in the direction of an arrow S. The advantage of this arrangement is that a number of doses can be irradiated at the same time within a short time period.

It is to be understood that while the present invention has been illustrated and described in relation to several potentially preferred embodiments, such embodiments are illustrative only and that the present invention is in no event to be limited thereto. Rather, it is contemplated that modifications and variations embodying the principle of the present invention will no doubt occur to those skilled in the art. It is therefore contemplated and intended that the invention shall extend to all such modifications and variations as may incorporate the broad principle of this invention within the full spirit and scope of the claims appended hereto. In particular, although material substitution, simple function addition, simple shape change and dimension change may be proposed variously, it is apparent that these shall fall within the scope of the right of the invention.

As described above, the present invention provides an electron beam irradiator designed to irradiate electron beams in a wide area at a low energy by using field emitter tips so that electron beams can be irradiated in a wide area without using an electromagnet as well as in a high current density without using a heater such as a filament or an additional power supply, thereby ensuring a simplified structure as well as a reduced size.

The invention claimed is:

1. An electron beam irradiator comprising:
    a vacuum chamber having a beam irradiation window formed longitudinally in an outer periphery of the vacuum chamber;
    a cathode placed centrally and longitudinally inside the vacuum chamber, and having a field emitter tip formed on the cathode, corresponding to the beam irradiation window;
    a high voltage supply placed at one end of the vacuum chamber, and adapted to apply high voltage toward the cathode;
    a first support supporting one end of the cathode, the first support including a first insulator through which a high voltage supply pin of the high voltage supply is inserted into a pin insert hole formed at one end of the cathode;
    and a second support supporting the other end of the cathode, the second support including a second insulator having an insert groove into which an insert protrusion formed at the other end of the cathode is inserted.

2. The electron beam irradiator according to claim 1, wherein the field emitter tip is made of a carbon nanotube.

3. The electron beam irradiator according to claim 1, wherein the cathode is of a rod-shaped structure having a circular cross-section, and includes a field emitter tip shaped as a strip formed longitudinally in an outer periphery of the rod-shaped structure.

4. The electron beam irradiator according to claim 3, wherein the field emitter tip is formed along the circular cross-section of the cathode to radially emit electron beams.

5. The electron beam irradiator according to claim 3, further comprising:
    fixing flanges integrally provided at both ends of the vacuum chamber;
    a first vacuum flange coupled with one of the fixing flanges, and having a high voltage supply; and
    a second vacuum flange coupled with the other one of the fixing flanges.

6. The electron beam irradiator according to claim 3, wherein the vacuum chamber is cylindrical, with a plurality of beam irradiation windows formed in an outer periphery thereof, and wherein the cathode placed inside the vacuum chamber has field emitter tips formed in an outer periphery of the cathode, corresponding to the beam irradiation windows of the vacuum chamber, respectively.

7. The electron beam irradiator according to claim 1, further comprising:
    fixing flanges integrally provided at both ends of the vacuum chamber;
    a first vacuum flange coupled with one of the fixing flanges, and having a high voltage supply; and
    a second vacuum flange coupled with the other one of the fixing flanges.

8. The electron beam irradiator according to claim 7, wherein the second insulator of the second support has a plurality of prominences and depressions formed on the second insulator to extend surface passages thereof in order to prevent insulation breakdown under high voltage.

9. The electron beam irradiator according to claim 1, wherein the beam irradiation window comprises:

a base plate fixed to the vacuum chamber, slightly protruded from the vacuum chamber to the outside, and having an elongated rectangular slit formed in a central area thereof;

a metal wire inserted into an insert groove formed in an outer periphery of the slit of the base plate;

a metal foil placed on the metal wire, and having an area slightly larger than an area surrounded by the metal wire; and a cover plate coupled with the base plate, corresponding to the slit of the base plate, and having a beam irradiation slit corresponding to the slit in the central area of the base plate.

10. The electron beam irradiator according to claim 1, wherein the vacuum chamber is cylindrical, with a plurality of beam irradiation windows formed in an outer periphery thereof, and wherein the cathode placed inside the vacuum chamber has field emitter tips formed in an outer periphery of the cathode, corresponding to the beam irradiation windows of the vacuum chamber, respectively.

11. The electron beam irradiator according to claim 10, wherein the electron beam windows are formed at both sides of the vacuum chamber to provide treatment to an object that moves linearly outside the vacuum chamber.

12. The electron beam irradiator according to claim 10, wherein the electron beam windows are formed at three sides of the vacuum chamber to provide treatment to an object that moves around the vacuum chamber.

13. The electron beam irradiator according to claim 10, wherein the electron beam windows are formed at four sides of the vacuum chamber to provide treatment to a cylindrical object while the vacuum chamber is rotated inside the cylindrical object.

14. An electron beam irradiator comprising:

a vacuum chamber having a plurality of beam irradiation windows formed longitudinally in an outer peripheral area of the vacuum chamber;

a cathode placed centrally and longitudinally inside the vacuum chamber, and having at least one linear area formed thereon and a plurality of field emitter tips formed on the linear area, corresponding to the beam irradiation windows, respectively;

a high voltage supply placed at one end of the vacuum chamber, and adapted to apply high voltage toward the cathode;

a first support supporting one end of the cathode, the first support including a first insulator through which a high voltage supply pin of the high voltage supply is inserted into a pin insert hole formed at one end of the cathode;

and a second support supporting the other end of the cathode, the second support including a second insulator having an insert groove into which an insert protrusion formed at the other end of the cathode is inserted into the insert groove to support the cathode.

15. The electrode beam irradiator according to claim 14, wherein the vacuum chamber has at least one linear area opposed in parallel to the linear area of the cathode, in which the beam irradiation windows are formed.

* * * * *

UNITED STATES PATENT AND TRADEMARK OFFICE
CERTIFICATE OF CORRECTION

PATENT NO. : 7,671,522 B2  Page 1 of 1
APPLICATION NO. : 10/591894
DATED : March 2, 2010
INVENTOR(S) : Lee et al.

It is certified that error appears in the above-identified patent and that said Letters Patent is hereby corrected as shown below:

Column 1, Lines 22-23, "previous one can be realized." should read -- previous one. --

Column 6, Line 2, "support 3" should read -- first support 3 --

Column 10, Lines 23-24, Claim 14, "is inserted into the insert groove to support the cathode." should read -- is inserted. --

Signed and Sealed this

Twentieth Day of July, 2010

David J. Kappos
*Director of the United States Patent and Trademark Office*